United States Patent [19]

Kohno et al.

[11] Patent Number: 5,643,938
[45] Date of Patent: Jul. 1, 1997

[54] PYRAZOLOPYRIDINE COMPOUNDS FOR THE TREATMENT OF ANEMIA

[75] Inventors: Yutaka Kohno; Itsuo Nagatomi, both of Osaka; Kaori Hanaoka, Kyoto, all of Japan

[73] Assignee: Fujisawa Pharmaceutical Co., Ltd., Osaka, Japan

[21] Appl. No.: 338,539

[22] PCT Filed: Jun. 7, 1993

[86] PCT No.: PCT/JP93/00762

§ 371 Date: Dec. 8, 1994

§ 102(e) Date: Dec. 8, 1994

[87] PCT Pub. No.: WO93/25205

PCT Pub. Date: Dec. 23, 1993

[30] Foreign Application Priority Data

Jun. 10, 1992 [GB] United Kingdom .............. 9212264
Jul. 24, 1992 [GB] United Kingdom .............. 9215794

[51] Int. Cl.⁶ .................................................. A01N 43/56
[52] U.S. Cl. ........................................ 514/403; 514/406
[58] Field of Search ................................. 514/310, 403, 514/406

[56] References Cited

U.S. PATENT DOCUMENTS

| | | | |
|---|---|---|---|
| 5,102,878 | 4/1992 | Shiokawa et al. | 514/212 |
| 5,338,743 | 8/1994 | Shiokawa et al. | 514/300 |
| 5,459,031 | 10/1995 | Blumen et al. | 435/3 |

*Primary Examiner*—Jeffrey C. Mullis
*Attorney, Agent, or Firm*—Oblon, Spivak, McClelland, Maier & Neustadt, P.C.

[57] ABSTRACT

The present invention relates to a pharmaceutical composition for the prevention and/or the treatment of anemia in a human being or an animal which comprises, as an active ingredient, a pyrazolopyridine compound of the following formula:

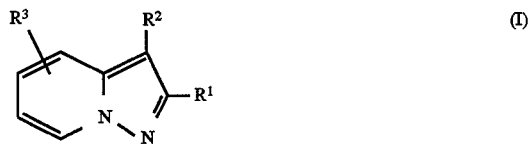

wherein $R^1$ is lower alkyl, etc, $R^2$ is a group of the formula:

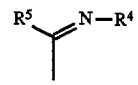

(wherein $R^4$ is protected amino, etc and $R^5$ is hydrogen, etc); etc, and $R^3$ is hydrogen, etc, or a pharmaceutically acceptable salt thereof in admixture with a pharmaceutically acceptable carrier or excipient, etc.

6 Claims, No Drawings

PYRAZOLOPYRIDINE COMPOUNDS FOR THE TREATMENT OF ANEMIA

This application is a 371 of PCT/JP93/00762 filed Jun. 7, 1993.

TECHNICAL FIELD

The present invention relates to a new medical use of the pyrazolopyridine compound or a pharmaceutically acceptable salt thereof.

BACKGROUND ART

Some pyrazolopyridine compounds are known to be useful as psychostimulant, antihypertensive agent, remedy for renal insufficiency, diuretic, and the like (e.g. EP-0299209, EP-0379979, etc), but up to now it is not known that the pyrazolopyridine compound is useful for the prevention and/or the treatment of anemia.

DISCLOSURE OF INVENTION

The present invention relates to a new use of the pyrazolopyridine compound or a pharmaceutically acceptable salt thereof.

More particularly, it relates to the utility of the pyrazolopyridine compound for the prevention and/or the treatment of anemia in a human being or an animal.

Accordingly, one object of the present invention is to provide a pharmaceutical composition for the prevention and/or the treatment of anemia in a human being or an animal comprising, as an active ingredient, the pyrazolopyridine compound or a pharmaceutically acceptable salt thereof.

Another object of the present invention is to provide a method for the prevention and/or the treatment of anemia in a human being or an animal which comprises administering the pyrazolopyridine compound to a human being or an animal.

A further object of the present invention is to provide a use of the pyrazolopyridine compound for the manufacture of a medicament for the prevention and/or the treatment of anemia in a human being or an animal.

The inventors of the present invention have found the pyrazolopyridine compound or a pharmaceutically acceptable salt thereof has been useful for the prevention and/or treatment of anemia in a human being or an animal and have completed the present invention.

The inventors have also found the pyrazolopyridine compound of the present invention has increased the production of erythropoietin.

The pyrazolopyridine compound to be used in the present invention is shown by the following formula (I) :

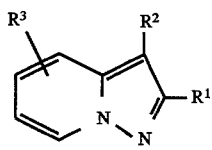

(I)

wherein $R^1$ is lower alkyl, aryl which may have one or more suitable substituent(s) or a heterocyclic group, $R^2$ is a group of the formula:

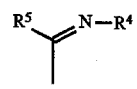

(wherein $R^4$ is protected amino or hydroxy and $R^5$ is hydrogen or lower alkyl);

cyano;

a group of the formula:

(wherein $R^6$ is an acyl group, or a group of the formula:

wherein $R_N$ is N-containing heterocyclic group which may have one or more suitable substituent(s) selected from the group consisting of lower alkyl, lower alkoxy(lower)alkyl, acyloxy(lower)alkyl, carboxy, protected carboxy and acyl(lower)alkyl, and A is lower aliphatic hydrocarbon group which may have one or more suitable substituent(s));

amidated carboxy;

unsaturated heterocyclic group which may have one or more suitable substituent(s);

amino or protected amino; and $R^3$ is hydrogen, lower alkyl, lower alkoxy or halogen, or a pharmaceutically acceptable salt thereof.

Some of the compound (I) are known compounds and they are disclosed, for example, in EP-0299209, EP-0379979, EP-0467248, etc.

In the compound (I), the following compound (Ia) novel.

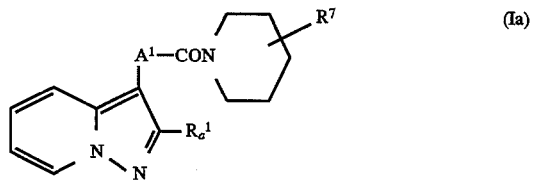

(Ia)

wherein $R_a^1$ is aryl, $R^7$ is acyl(lower)alkyl, and $A^1$ is lower alkenylene.

The compound. (Ia) or a salt thereof of the present invention can be prepared by the following reaction schemes.

Process 1

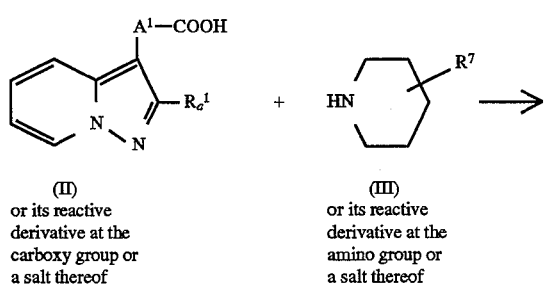

(II)
or its reactive
derivative at the
carboxy group or
a salt thereof (III)
or its reactive
derivative at the
amino group or
a salt thereof

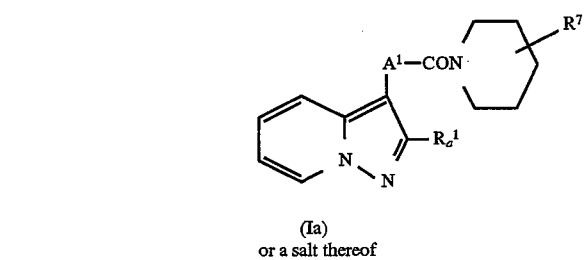

(Ia)
or a salt thereof

Process 2

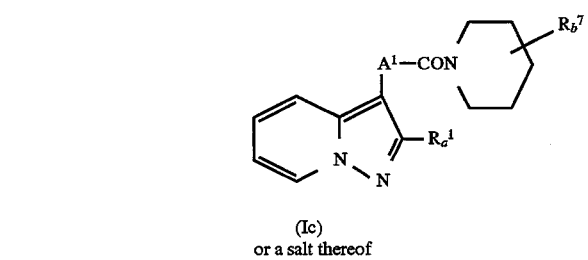

(Ib)
or a salt thereof elimination reaction
of the carboxy
protective group
→

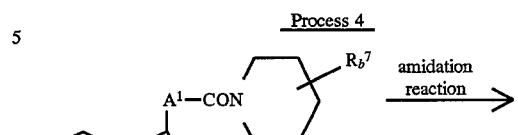

(Ic)
or a salt thereof

Process 3

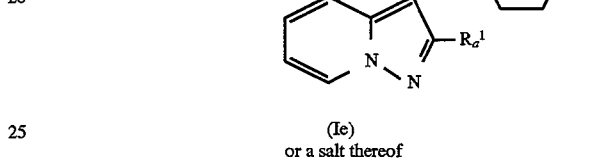

(IV)
or a salt thereof oxidation
reaction
→

(Id)
or a salt thereof

-continued
Process 1

Process 4

(Ic)
or its reactive derivative
at the carboxy group
or a salt thereof amidation
reaction
→

(Ie)
or a salt thereof wherein $R_a^1$, $R^7$ and $A^1$ are each as defined above,
$R_a^7$ is protected carboxy(lower)alkyl,
$R_b^7$ is carboxy(lower)alkyl,
$R_c^7$ is formyl(lower)alkyl or carboxy(lower)alkyl,
$R_d^7$ is amidated carboxy(lower)alkyl, and
$R^8$ is hydroxy(lower)alkyl.

The reactions in above-mentioned Processes 1 to 4 can be carried out according to the procedures disclosed in Examples mentioned later in the present specification or the similar manners thereto.

It is to be noted that the object compound (I) may include the geometrical isomer(s) due to the double bond(s) and/or the stereo isomer(s) due to the asymmetric carbon atom(s). In this regard, one isomer can be converted to another according to a conventional manner in this field of the art.

Suitable pharmaceutically acceptable salts of the object compound (I) are conventional ones and include a metal salt such as an alkali metal salt (e.g. sodium salt, potassium salt, etc) and an alkaline earth metal salt (e.g. calcium salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumalate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "lower aliphatic hydrocarbon group" may include lower alkyl, lower alkenyl, lower alkynyl as explained below and the like.

Suitable "lower alkyl" may include straight or branched ones such as methyl, ethyl, propyl, isopropyl, butyl, t-butyl, pentyl, hexyl or the like, in which the preferred one may be $(C_1-C_4)$alkyl and the more preferred one may be methyl, ethyl, propyl and isopropyl.

Suitable "lower alkenyl" may include straight or branched ones such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, 5-hexenyl or the like, in which the preferred one may be $(C_2-C_4)$alkenyl and the more preferred one may be vinyl, 1-methylvinyl, 2-methylvinyl and 1,3-butadienyl.

Suitable "lower alkynyl" may include straight or branched ones such as ethynyl, 1-propynyl, 1-methylethynyl, 2-butynyl, 2-methyl-3-butynyl, 2-pentynyl, 1-hexynyl or the like, in which the preferred one may be $(C_2-C_4)$alkynyl and the more preferred one may be ethynyl.

Aforesaid "lower aliphatic hydrocarbon group" may have one or more (preferably one to three) suitable substituent(s) such as halogen (e.g. chloro, bromo, fluoro, iodo) or the like.

Suitable "protected amino" may include amino substituted with the conventional amino protective group such as lower alkylamino (e.g. methylamino, ethylamino, propylamino, butylamino, t-butylamino, pentylamino, hexylamino, etc.), di(lower)alkylamino (e.g. dimethylamino, diethylamino, N-ethylpropylamino, dibutylamino, N-(t-butyl)pentylamino, dihexylamino, etc), acylamino explained below or the like.

Suitable "acylamino" may include ureido; lower alkanoylamino (e.g. formylamino, acetylamino, propionylamino, butyrylamino, isobutyrylamino, pivaloylamino, hexanoylamino, etc), lower alkoxycarbonylamino (e.g. methoxycarbonylamino, ethoxycarbonylamino, propoxycarbonylamino, t-butoxycarbonylamino, pentyloxycarbonylamino, hexyloxycarbonylamino, etc), lower alkoxycarbonyl(lower)alkanoylamino (e.g. methoxycarbonylacetylamino, ethoxycarbonylacetylamino, 2-(propoxycarbonyl)propionylamino, 4-(t-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc), lower alkanesulfonylamino (e.g. methanesulfonylamino, ethanesulfonylamino, propanesulfonylamino, butanesulfonylamino, t-butanesulfonylamino, pentanesulfonylamino, hexanesulfonylamino, etc) and the like.

Said "lower alkanoylamino" may have suitable substituent(s) such as di(lower)alkylamino (e.g. dimethylamino, N-methyl-N-ethylamino, dipropylamino, di-t-butylamino, N-pentyl-N-hexylamino, etc); cyclic amino group (e.g. piperidino, etc) which may have lower alkyl; or the like, and suitable examples of said "lower alkanoylamino having suitable substituent(s)" may include lower alkanoylamino having di(lower)alkylamino [e.g. dimethylaminocarbonylamino, 2-dimethylaminoacetylamino, 2-(N-methyl-N-ethylamino) acetylamino, 2-dimethylaminopropionylamino, 3-dipropylaminobutyrylamino, 2-(di-t-butylamino)-2-methylpropionylamino, 2-dimethylaminomethyl-2-methylpropionylamino, 6-(N-pentyl-N-hexylamino) hexanoylamino, etc];

lower alkanoylamino having cyclic amino group which may have lower alkyl [e.g. piperidinocarbonylamino, 2-piperidinoacetylamino, 2-(2-methylpiperidino) acetylamino, 2-(2-ethylpiperidino)acetylamino, 2-piperidinopropionylamino, 3-(2-ethylpiperidino) butyrylamino, 2-(4-ethylpiperidino-2-methylpropionylamino, 2-piperidinomethyl-2-methylpropionylamino, 6-(3-propylpiperidino) hexanoylamino, etc]; and the like.

In aforesaid "acylamino", the preferred one may be ureido, $(C_1-C_4)$alkanoylamino, $(C_1-C_4)$alkoxycarbonyl-$(C_1-C_4)$alkanoylamino, di$(C_1-C_4)$alkylamino$(C_1-C_4)$ alkanoylamino, $(C_1-C_4)$alkylpiperidino$(C_1-C_4)$ alkanoylamino, $(C_1-C_4)$alkoxycarbonylamino, $(C_1-C_4)$ alkanesulfonylamino, $(C_1-C_4)$alkylamino and di$(C_1-C_4)$ alkylamino, in which the more preferred one may be ureido, acetylamino, 2-(ethoxycarbonyl)acetylamino, 2-dimethylaminoacetylamino, 2-(2-ethylpiperidino) acetylamino, methoxycarbonylamino, methanesulfonytamino, methylamino and dimethylamino.

Suitable "an acyl group" may include lower alkanoyl (e.g. formyl, acetyl, propionyl, butyryl, isobutyryl, pivaloyl, hexanoyl, etc); carboxy; protected carboxy; and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc) which may have N-containing heterocyclic group as explained below and the like;

amidated carboxy, in which suitable amidated carboxy may include N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc);

N-(higher)alkylcarbamoyl (e.g. N-heptylcarbamoyl, N-(2-methylheptyl)carbamoyl, N-nonylcarbamoyl, N-decanylcarbamoyl, N-tricyclo[$3.3.1.1^{3,7}$] decanylcarbamoyl, N-undecanylcarbamoyl, N-(bicyclo [4.3.2]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl) carbamoyl, N-pentyl-N-hexylcarbamoyl, etc];

N-lower alkyl-N-ar(lower)alkylcarbamoyl (e.g. N-methyl-N-benzylcarbamoyl, etc); or the like.

Suitable "N-containing heterocyclic group" in $R_N$ may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g. 1H-azepinyl, etc) pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl, etc) etc;

saturated 3 to 8-membered (more preferably 5 to 7 membered) heteromonocyclic group containing 1 to 4 nitrogen atom(s), for example, perhydroazepinyl (e.g. perhydro-1H-azepinyl, etc) pyrrolidinyl, imidazolidinyl, piperidino, piperazinyl, etc;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc;

saturated condensed heterocyclic group containing 1 to 4 nitrogen atom(s), for example, 7-azabicyclo[2.2.1] heptyl, 3-azabicyclo[3.2.2]nonanyl, etc;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc), etc;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazoly (e.g. 1,2,3-thiadiazolyl, 1,2,4-thiadiazolyl, 1,3,4-thiadiazolyl, 1,2,5-thiadiazolyl, etc), dihydrothiazinyl, etc;

saturated 3 to 8-membered (more preferably 5 or 6-membered) heteromonocyclic group containing 1 to 2 sulfur atom(s) and 1 to 3 nitrogen atom(s), for example, thiazolidinyl, etc;

unsaturated condensed heterocyclic group containing 1 to 2 sulfur atom(s) and 1 to 3 nitrogen atom(s), for example, benzothiazolyl, benzothiadiazolyl, etc; in which the preferred one may include saturated 3 to 8 membered heteromonocyclic group containing 1 to 4 nitrogen atom(s), saturated condensed heterocyclic group containing 1 to 4 nitrogen atom(s), and saturated 3 to 8 membered heteromonocyclic group containing 1 to 2 oxygen atom(s) and 1 to 3 nitrogen atom(s).

"N-containing heterocyclic group" thus defined may have one or more (preferably 1 to 4) suitable substituent(s) selected from the group consisting of lower alkyl as mentioned above; lower alkoxy(lower)alkyl (e.g. methoxymethyl, 2-methoxyethyl, 1-ethoxyethyl, 3-propoxypropyl, 2-(t-butoxy)butyl, 5-pentyloxypentyl, 3-hexyloxyhexyl, etc); acyloxy(lower)alkyl such as lower alkanoyloxy(lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc) or the like; protected carboxy such as lower alkoxycarbonyl as mentioned above; carboxy; acyl(lower)alkyl such as lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc), carboxy(lower)alkyl (e.g. carboxymethyl, 1-carboxyethyl, 2-carboxypropyl, 1-(carboxymethyl)ethyl, 4-carboxybutyl, 3-carboxypentyl, 2-carboxyhexyl, etc) or protected carboxy(lower)alkyl, in which the preferred "protected carboxy(lower)alkyl" may be esterified carboxy(lower)alkyl, the most preferred one may be lower alkoxycarbonyl(lower)alkyl (e.g. methoxycarbonylmethyl, 2-methoxycarbonylethyl, 1-ethoxycarbonylethyl, 2-propoxycarbonyipropyl, 1-(methoxycarbonylmethyl)ethyl, 4-t-butoxycarbonylbutyl, 3-pentyloxycarbonylpentyl, 2-hexyloxycarbonylhexyl, etc); or the like.

In aforesaid "N-containing heterocyclic group which may have one or more suitable substituent(s)", the more preferred one may include piperidino which may have 1 to 4 suitable substituent(s) selected from a group consisting of $(C_1-C_4)$ alkyl, $(C_1-C_4)$alkoxy$(C_1-C_4)$alkyl, $(C_1-C_4)$alkanoyloxy $(C_1-C_4)$alkyl, $(C_1-C_4)$alkoxycarbonyl, carboxy, $(C_1-C_4)$ alkanoyl$(C_1-C_4)$alkyl, carboxy$(C_1-C_4)$alkyl and $(C_1-C_4)$ alkoxycarbonyl$(C_1-C_4)$alkyl (e.g. piperidino, 2-methylpiperidino, 2-ethylpiperidino, 3-ethylpiperidino, 4-ethylpiperidino, 2-propylpiperidino, 4-isopropylpiperidino, 2-butylpiperidino, 3-(t-butyl) piperidino, 4-pentylpiperidino, 2-hexylpiperidino, 2,2,6,6-tetramethylpiperidino, 2,2-dimethyl-6,6-diethylpiperidino, 2-methoxymethylpiperidino, 2-(2-methoxyethyl)piperidino, 2-(1-ethoxyethyl)piperidino, 3-(3-propoxypropyl) piperidino, 4-{2-(t-butoxy)butyl}piperidino, 2-(5-pentyloxypentyl)piperidino, 3-(3-hexyloxyhexyl) piperidino, 2-acetoxymethylpiperidino, 3-(1-acetoxyethyl) piperidino, 2-(2-acetoxyethyl)piperidino, 3-(2-propionyloxyethyl)piperidino, 4-(3-propionyloxpropyl) piperidino, 2-(2-butyryloxybutyl)piperidino, 3-(4-pivaloyloxypentyl)piperidino, 2-(6-hexanoyloxyhexyl) piperidino, 2-methoxycarbonylpiperidino, 2-ethoxycarbonylpiperidino, 2-propoxycarbonylpiperidino, 3-butoxycarbonylpiperidino, 4-(t-butoxycarbonyl) piperidino, 2-pentyloxycarbonylpiperidino, 2-hexyloxycarbonylpiperidino, 2-carboxypiperidino, 3-carboxypiperidino, 4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl) piperidino, 3-(2-butyrylbutyl)piperidino, 2-[1-(formylmethyl)ethyl]piperidino, 2-carboxymethylpiperidino, 2-(1-carboxyethyl)piperidino, 3-(2-carboxypropyl)piperidino, 4-[1-(carboxymethyl)ethyl] piperidino, 2-(4-carboxybutyl)piperidino, 2-methoxycarbonylmethylpiperidino, 2-(2-methoxycarbonylethyl)piperidino, 3-(1-ethoxycarbonylethyl)piperidino, 4-(2-propoxycarbonylpropyl)piperidino, 2-[1-(methoxycarbonylmethyl)ethyl]piperidino, 2-(4-t-butoxycarbonylbutyl)piperidino, etc);

pyrrolidin-1-yl which may have $(C_1-C_4)$alkoxy$(C_1-C_4)$ alkyl (e.g. pyrrolidin-1-yl, 2-methoxymethylpyrrolidin-1-yl. 2-(2-methoxyethyl) pyrrolidin-1-yl, 2-(1-ethoxyethyl)pyrrolidin-1-yl, 3-(3-propoxypropylpyrrolidin-1-yl, 3-{2-(t-butoxy) butyl}pyrrolidin-1-yl, 2-(5-pentyloxypentyl) pyrrolidin-1-yl, 2-(3-hexyloxyhexyl)pyrrolidin-1-yl, etc);

perhydroazepin-1-yl (e.g. perhydro-1H-azepin-1-yl, etc);

piperazin-1-yl which may have $(C_1-C_4)$alkyl (e.g. piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(t-butyl)piperazin-1-yl, 4-pentylpiperazin-1-yl, 4-hexylpiperazin-1-yl, etc);

morpholino; 7-azabicyclo[2.2.1]heptan-7-yl; 3-azabicyclo[3.2.2]nonan-3-yl; and the like, and the most preferred one may include piperidino, 2-methylpiperidino, 2-ethylpiperidino, 3-ethylpiperidino, 4-ethylpiperidino, 2-propylpiperidino, 2,2,6,6-tetramethylpiperidino, 2-methoxymethylpiperidino, 2-(2-methoxyethyl) piperidino, 2-acetoxymethylpiperidino, 2-(2-acetoxyethyl)piperidino, 2-ethoxycarbonylpiperidino, 2-carboxypiperidino, 2-carboxymethylpiperidino, pyrrolidin-1-yl, 2-methoxymethylpyrrolidin-1-yl, perhydro-1H-azepin-1-yl, 4-methylpiperazin-1-yl, morpholino, 7-azabicyclo[2.2.1]heptan-7-yl, 3-azabicyclo[3.2.2]nonan-3-yl, and the like.

Suitable "aryl" may include phenyl, naphthyl, indenyl, anthryl and the like and said "aryl" may have one or more suitable substituent(s) such as halogen (e.g. fluoro, chloro, bromo, iodo), lower alkoxy (e.g. methoxy, ethoxy, propoxy, t-butoxy, pentyloxy, hexyloxy, etc), nitro, amino, protected amino as mentioned before or the like.

The preferred examples of "aryl which may have one or more suitable substituent(s)" may include phenyl which may have 1 to 3 suitable substituent(s) selected from a group consisting of halogen, ($C_1$–$C_4$)alkoxy, nitro, amino, ($C_1$–$C_4$) alkanoylamino, ($C_1$–$C_4$)alkoxycarbonylamino, ($C_1$–$C_4$) alkanesulfonylamino, ($C_1$–$C_4$)alkylamino and di($C_1$–$C_4$) alkylamino, in which the more preferred one may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino and phenyl having dimethylamino.

Suitable "a heterocyclic group" may include the ones as exemplified for "N-containing heterocyclic group" as mentioned above, unsaturated 3 to 8-membered (more preferably 5 or 6-membered) heteromonocyclic group containing an oxygen atom, for example, furyl, etc;

unsaturated 3 to 8-membered (more preferably 5 or 6-membered) heteromonocyclic group containing an oxygen atom and 1 to 2 sulfur atom(s), for example, dihydrooxathiinyl, etc;

unsaturated condensed heterocyclic group containing 1 to 2 sulfur atom(s), for example, benzothienyl, benzodithiinyl, etc;

unsaturated condensed heterocyclic group containing an oxygen atom and 1 to 2 sulfur atom(s), for example, benzoxathiinyl, etc and the like, in which the preferred one may be unsaturated 3 to 8 membered heteromonocyclic group containing 1 to 4 nitrogen atom(s), the more preferred one may be pyridyl and the most preferred one may be 2-pyridyl, 3-pyridyl and 4-pyridyl.

Suitable "lower alkoxy" may include methoxy, ethoxy, propoxy, isopropoxy, butoxy, t-butoxy, pentyloxy, hexyloxy and the like.

Suitable "halogen" may include fluoro, chloro, bromo and iodo.

Suitable "unsaturated heterocyclic group" in "unsaturated heterocyclic group which may have one or more suitable substituent(s)" may include unsaturated, monocyclic or polycyclic heterocyclic group containing at least one hetero atom such as nitrogen, oxygen, sulfur or the like.

Suitable examples of said "unsaturated heterocyclic group" may include:

unsaturated 3 to 8-membered (more preferably 5 to 7-membered) heteromonocyclic group containing 1 to 4 nitrogen atom(s), for example, azepinyl (e.g. 1H-azepinyl, etc) pyrrolyl, pyrrolinyl, imidazolyl, pyrazolyl, pyridyl, dihydropyridyl (e.g. 1,2-dihydropyridyl, 1,4-dihydropyridyl, etc), tetrahydropyridyl (e.g. 1,2,3,6-tetrahydropyridyl, etc) pyrimidinyl, dihydropyrimidinyl (e.g. 1,2-dihydropyrimidinyl, etc), pyrazinyl, pyridazinyl, dihydropyridazinyl (e.g. 2,3-dihydropyridazinyl, 1,4-dihydropyridazinyl, etc), tetrahydropyridazinyl (e.g. 2,3,4,5-tetrahydropyridazinyl, etc) triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl, etc), etc;

unsaturated condensed heterocyclic group containing 1 to 4 nitrogen atom(s), for example, indolyl, isoindolyl, indolizinyl, benzimidazolyl, quinolyl, dihydroquinolyl (e.g. 2,3-dihydroquinolyl, etc) isoquinolyl, indazolyl, benzotriazolyl, etc;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, dihydroisoxazolyl (e.g. 2,5-dihydroisoxazolyl, etc) oxadiazolyl (e.g. 1,2,4-oxadiazolyl, 1,3,4-oxadiazolyl, 1,2,5-oxadiazolyl, etc), etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, dihydrothiazolyl (e.g. 2,3-dihydrothiazolyl, etc) isothiazolyl, thiadiazolyl (e.g. 1,2,3-thiadiazolyl, 1,2,4-thiadiazolyl, 1,3,4-thiadiazolyl, 1,2,5-thiadiazolyl, etc), dihydrothiazinyl, etc;

unsaturated condensed heterocyclic group containing 1 to 2 sulfur atom(s) and 1 to 3 nitrogen atom(s), for example, benzothiazolyl, benzothiadiazolyl, (e.g. benzo[d][1,2,3]thiadiazolyl, etc), imidazothiadiazolyl (e.g. 5H-imidazo[2,1-b][1,3,4]thiadiazolyl, etc), etc;

unsaturated 3 to 8-membered (more preferably 5 or 6-membered) heteromonocyclic group containing 1 to 2 sulfur atom(s), for example, thienyl, dihydrodithiinyl, etc;

unsaturated 3 to 8-membered (more preferably 5 or 6-membered) heteromonocyclic group containing an oxygen atom, for example, furyl, etc;

unsaturated 3 to 8-membered (more preferably 5 or 6-membered) heteromonocyclic group containing an oxygen atom and 1 to 2 sulfur atom(s), for example, dihydrooxathiinyl, etc;

unsaturated condensed heterocyclic group containing 1 to 2 sulfur atom(s), for example, benzothienyl, benzodithiinyl, etc;

unsaturated condensed heterocyclic group containing an oxygen atom and 1 to 2 sulfur atom(s) for example, benzoxathiinyl, etc and the like, in which the preferred one may be unsaturated heterocyclic group containing at least one nitrogen atom as hetero atom, the more preferred one may be unsaturated 3 to 8-membered heteromonocyclic group containing 1 to 4 nitrogen atom(s) and unsaturated condensed heterocyclic group containing 1 to 2 sulfur atom(s) and 1 to 3 nitrogen atom(s), the much more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl and imidazothiadiazolyl, and the most preferred one may be pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl, and imidazo[2,1-b][1,3,4]thiadiazolyl.

Aforesaid "unsaturated heterocyclic group" may have one or more (preferably 1 to 4) suitable substituent(s) such as lower alkyl (e.g. methyl, ethyl, propyl, isopropyl, butyl, t-butyl, pentyl, hexyl, etc) which may have one or more (preferably 1 to 4) suitable substituent(s) as explained below; carboxy(lower)alkenyl (e.g. 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc); amino; di(lower) alkylamino (e.g. dimethylamino, N-methylethylamino, dipropylamino, N-butyl-(2-methylbutyl)amino, N-pentylhexylamino, etc); halogen (e.g. fluoro, chloro, bromo, iodo, etc); lower alkoxy (e.g. methoxy, ethoxy, propoxy, isopropoxy, butoxy, t-tuboxy, pentyloxy, hexyloxy, etc); oxo; hydroxy; cyano; an acyl group as explained below; or the like.

Suitable "an acyl group" may include lower alkanoyl (e.g. formyl, acetyl, propionyl, butyryl, isobutyryl, pivaloyl, hexanoyl, etc), carboxy, protected carboxy, and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, t-butoxycarbonyl, pentyloxycarbonyl, hexyloxycarbonyl, etc) and the like;

amidated carboxy, in which suitable amidated carboxy may include carbamoyl, N,N-di(lower)alkylcarbamoyl wherein two lower alkyl groups may bond to each other to form 3 to 6-membered ring (e.g. N,N-dimethylcarbamoyl, N-methyl-N-ethylcarbamoyl, N,N-diethylcarbamoyl, N,N-dipropylcarbamoyl, N-butyl-N-t-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc) and the like; or the like.

Suitable examples of "suitable substituent(s)" of aforesaid "lower alkyl which may have one or more suitable substituent(s)" may include hydroxy, aforesaid halogen, aforesaid lower alkoxy, aforesaid an acyl group, and the like.

Suitable examples of said "lower alkyl having one or more suitable substituent(s)" may include lower alkyl having hydroxy and halogen (e.g. 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl, etc);

hydroxy(lower)alkyl (e.g. hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc);

lower alkoxy(lower)alkyl (e.g. methoxymethyl, ethoxymethyl, 2-ethoxyethyl, 1-propoxyethyl, 3-isopropoxypropyl, 2-butoxybutyl, 1-t-butoxymethyl-1-methylethyl, 5-pentyloxypentyl, hexyloxymethyl, 3-hexyloxyhexyl, etc);

acyl(lower)alkyl, in which the preferred one may be carboxy(lower)alkyl (e.g. carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc), and protected carboxy(lower) alkyl, in which the preferred one may be esterified carboxy(lower)alkyl and amidated carboxy(lower) alkyl, the more preferred one may be lower alkoxycarbonyl(lower)alkyl (e.g. methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-t-butoxycarbonylmethyl-1-methylethyl, 5-pentyloxycarbonylpentyl, hexyloxycarbonylmethyl, 3-hexyloxycarbonylhexyl, etc), carbamoyl(lower)alkyl (e.g. carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc), N,N-di (lower)alkylcarbamoyl(lower)alkyl in which two lower alkyl groups on nitrogen atom may bond to each other to form 3 to 6-membered ring [e.g. N,N-dimethylcarbamoylmethyl, 2-(N,N-dimethylcarbamoyl)ethyl, 2-(N-methyl-N-ethytcarbamoyl)ethyl, 3-(N-methyl-N-ethylcarbamoyl) propyl, 2-(N,N-dipropylcarbamoyl)-1-methylethyl, 4-(N,N-dipropylcarbamoyl)butyl, 1-(N,N-dimethylcarbamoyl)methyl-1-methylethyl, 5-(N-pentyl-N-hexylcarbamoyl)pentyl, 3-(N-pentyl-N-hexyl)hexyl, (1-aziridinylcarbonyl)methyl, 2-(1-azetidinylcarbonyl)ethyl, 2-(piperidinocarbonyl)ethyl, 3-(1-pyrrolidinylcarbonyl)propyl, 2-(1-piperidinocarbonyl)-1-methylethyl, 4-(1-azetidinylcarbonyl)butyl, 1-(1-aziridinylcarbonyl) methyl-1-methylethyl, 3-(1-pyrrolidinylcarbonyl) pentyl, 6-(piperidinocarbonyl)hexyl, etc]; and the like.

The preferred substituent of "unsaturated heterocyclic group" may be lower alkyl, lower alkyl having hydroxy and halogen, hydroxy(lower)alkyl, lower alkoxy(lower)alkyl, carboxy(lower)alkyl, lower alkoxycarbonyl(lower)alkyl, carbamoyl(lower)alkyl, N,N-di(lower)alkylcarbamoyl (lower)alkyl wherein two lower alkyl groups on nitrogen atom may bond to each other to form 3 to 6-membered ring, carboxy(lower)alkenyl, di(lower)alkylamino, halogen, lower alkoxy, oxo, carboxy, lower alkoxycarbonyl, lower alkanoyl, amino, cyano and hydroxy, in which the more preferred one may be $(C_1-C_4)$alkyl, $(C_1-C_4)$alkyl having hydroxy and halogen, hydroxy $(C_1-C_4)$alkyl, $(C_1-C_4)$alkoxy$(C_1-C_4)$alkyl, carboxy $(C_1-C_4)$alkyl, $(C_1-C_4)$alkoxycarbonyl$(C_1-C_4)$alkyl, carbamoyl$(C_1-C_4)$alkyl, N,N-di$(C_1-C_4)$ alkylcarbamoyl$(C_1-C_4)$alkyl, piperidinocarbonyl $(C_1-C_4)$alkyl, carboxy$(C_2-C_4)$alkenyl, di$(C_1-C_4)$ alkylamino, halogen, $(C_1-C_4)$alkoxy, oxo, carboxy, $(C_1-C_4)$alkoxycarbonyl, $(C_1-C_4)$alkanoyl, amino, cyano and hydroxy, and the most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

Aforesaid "unsaturated heterocyclic group" in "unsaturated heterocyclic group which may have one or more suitable substituent(s)" may have one or more (preferably 1 to 4) substituent(s) explained below as its "one or more suitable substituent(s)" in addition to the ones mentioned above, that is, amino(lower)alkyl; lower alkylamino (lower) alkyl; carboxy(lower)alkylamino(lower)alkyl; protected carboxy(lower)alkylamino(lower)alkyl; lower alkylamino (lower)alkyl having hydroxy and aryloxy, protected amino (lower)alkyl; cyano(lower)alkyl; cyano(higher)alkyl; lower alkyl having heterocyclic group in which heterocyclic group may have one or more suitable substituent(s); higher alkyl having heterocyclic group, in which heterocyclic group may have one or more suitable substituent(s); ar(lower)alkyl; lower alkenyl; or heterocyclic group which may have one or more suitable substituent(s).

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, and the like, in which the preferred one may be amino $(C_1-C_4)$alkyl and the more preferred one may be 2-aminoethyl.

Suitable "lower alkylamino(lower)alkyl" may include mono- or di- (lower)alkylamino(lower)alkyl" such as methylaminomethyl, 2-(ethylamino)ethyl, 3-(propylamino) propyl, 2-(propylamino)butyl, 2-t-butylamino)-1,1-dimethylethyl, 4-pentylaminopentyl, 6-hexylaminohexyl, dimethylaminomethyl, 2-dimethylaminoethyl, 1(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, or the like; and the like, in which the preferred one may be di(lower)alkylamino(lower) alkyl, the more preferred one may be di$(C_1-C_4)$alkylamino $(C_1-C_4)$alkyl and the most preferred one may be 2-dimethylaminoethyl, 3-dimethylaminopropyt and 4-dimethylaminobutyl.

Suitable "carboxy(lower)alkylamino(lower)alkyl" may include carboxymethylaminomethyl, 2-(carboxymethylamino)ethyl, 2-(1-carboxyethylamino) ethyl, 3-(2-carboxypropylamino)propyl, 2-(3-carboxypropylamino )butyl, 2-(2-carboxy-1,1-dimethylethylamino)-1,1-dimethylethyl, 4-(5-carboxypentylamino)pentyl, 6-(3-carboxyhexylamino) hexyl, and the like, in which the preferred one may be carboxy$(C_1-C_4)$alkylamino$(C_1-C_4)$alkyl and the most preferred one may be 2-(carboxymethylamino)ethyl.

Suitable "protected carboxy" in "protected carboxy (lower)alkylamino(lower)alkyl" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc], lower alkanesulfonyl(lower)alkyl ester [e.g. 2-mesylethyl ester, etc] or mono(or di or tri)halo(lower)alkyl ester [e.g. 2-iodoethyl ester, 2,2,2-trichloroethyl ester, etc]; lower alkenyl ester [e.g. vinyl ester, allyl ester, etc]; lower alkynyl ester [e.g. ethynyl ester, propynyl ester, etc]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester, etc]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc]; or the like.

Suitable example of "protected carboxy(lower) alkylamino(lower)alkyl" may be esterified carboxy(lower) alkylamino(lower)alkyl, in which the preferred one may be lower alkoxycarbonyl(lower)alkylamino(lower)alkyl such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, or the like; the more preferred one may be $(C_1-C_4)$alkoxycarbonyl$(C_1-C_4)$ alkylamino$(C_1-C_4)$alkyl, and the most preferred one may be 2-(ethoxycarbonylmethylamino)ethyl.

Suitable "lower alkylamino(lower)alkyl having hydroxy and aryloxy" may be aforesaid "lower alkylamino(lower) alkyl" having "hydroxy" and "aryloxy" (e.g. phenoxy, tolyloxy, naphthyloxy, etc) and suitable examples thereof may include 1-(1-naphthyloxy)-1-hydroxymethylaminomethyl, 2-(1-hydroxy-2-phenoxyethylamino)ethyl, 2-[2-hydroxy-3-(1-naphthyloxy) propylamino]ethyl, 2-[4-hydroxy-3-(p-tolyloxy) butylamino]propyl, 2-[4-hydroxy-1-(2-naphthyloxy) butylamino]-1,1-dimethylethyl, 4-[1-hydroxy-5-(1-naphthyloxy)pentylamino]pentyl, 6-[2-hydroxy-4-(2-naphthyloxy)hexylamino]hexyl, in which the preferred one may be $(C_1-C_4)$alkylamino$(C_1-C_4)$alkyl having hydroxy and naphthyloxy and the more preferred one may be 2-[2-hydroxy-3-(1-naphthyloxy)propylamino]ethyl.

Suitable "protected amino(lower)alkyl" may be acylamino(lower)alkyl.

Suitable example of the acylamino may be lower alkanoylamino [e.g. formylamino, acetylamino, propionylamino, hexanoylamino, pivaloylamino, etc], mono(or di or tri)halo (lower)alkanoylamino [e.g. chloroacetylamino, trifluoroacetylamino, etc], lower alkoxycarbonylamino [e.g. methoxycarbonylamino, ethoxycarbonylamino, tert-butoxycarbonylamino, tert-pentyloxycarbonylamino, hexyloxycarbonylamino, etc], mono(or di or tri)halo(lower) alkoxycarbonylamino [e.g. chloromethoxycarbonylamino, dichloroethoxycarbonylamino, trichloroethoxycarbonylamino, etc], aroylamino [e.g. benzoylamino, toluoylamino, xyloylamino, naphthoylamino, etc], ar(lower)alkanoylamino such as phenyl(lower)alkanoylamino [e.g. phenylacetylamino, phenylpropionylamino, etc], aryloxycarbonylamino [e.g. phenoxycarbonylamino, naphthyloxycarbonylamino, etc], aryloxy(lower)alkanoylamino such as phenoxy(lower) alkanoylamino [e.g. phenoxyacetylamino, phenoxypropionylamino, etc], arylglyoxyloylamino [e.g. phenylglyoxyloylamino, naphthylglyoxyloylamino, etc], ar(lower)alkoxycarbonylamino which may have suitable substituent(s) such as phenyl(lower)alkoxycarbonylamino which may have nitro or lower alkoxy [e.g. benzyloxycarbonylamino, phenethyloxycarbonylamino, p-nitrobenzyloxycarbonylamino, p-methoxybenzyloxycarbonylamino, etc], thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino [e.g. methylsulfonylamino, ethylsulfonylamino, propylsulfonylamino, isopropylsulfonylamino, pentylsulfonylamino, butylsulfonylamino, etc], arylsulfornylamino [e.g. phenylsulfonylamino, tolylsulfonylamino, xylylsulfonylamino, naphthylsulfonylamino, etc], ar(lower) alkylsulfonylamino such as phenyl(lower) alkylsulfonylamino [e.g. benzylsulfonylamino, phenethylsulfonylamino, benzhydrylsulfonylamino, etc], imido [e.g. 1,2-cyclohexanedicarboximido, succinimido, phthalimido, etc], and the like.

Preferred example of said "protected amino(lower)alkyl" may be imido(lower)alkyl such as phthalimidomethyl, 2-phthalimidoethyl, 1-(1,2-cyclohexanedicarboximido)

ethyl, 2-succinimidopropyl, 3-phthalimidobutyl, 2-(1,2-cyclohexanedicarboximido)-1,1-dimethylethyl, 5-phthalimidopentyl, 1-phthalimidohexyl, or the like, the more preferred one may be imido($C_1$–$C_4$)alkyl and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, 6-cyanohexyl and the like, in which the preferred one may be cyano($C_1$–$C_6$)alkyl and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoicosyl, and the like, in which the preferred one may be cyano($C_7$–$C_{16}$)alkyl and the more preferred one may be 7-cyanoheptyl, 8-cyanooctyl, 9-cyanononyl, 10-cyanodecyl and 12-cyanododecyl.

Suitable "lower alkyl" may be a straight or branched one such as methyl, ethyl, propyl, isopropyl, butyl, t-butyl, pentyl, hexyl or the like.

Suitable "lower alkenyl" may be a straight or branched one such as vinyl, allyl, 2-butenyl, 2-methyl-2-propenyl, 4-pentenyl, 3-hexenyl, or the like, in which the preferred one may be ($C_2$–$C_4$)alkenyl and the more preferred one may be vinyl.

Suitable "lower alkyl" in "lower alkyl having heterocyclic group, in which heterocyclic group may have one or more suitable substituent(s)" can be referred to the ones as exemplified before, and the preferred one may be ($C_1$–$C_6$)alkyl and the most preferred one may be methyl, ethyl, propyl, butyl, pentyl and hexyl.

Suitable "higher alkyl" in "higher alkyl having heterocyclic group, in which heterocyclic group may have one or more suitable substituent(s)" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl 12-ethylheptadecyl, icosyl and the like, in which the preferred one may be ($C_7$–$C_{16}$)alkyl, and the more preferred one may be heptyl, octyl, nonyl, decyl, and dodecyl.

Suitable "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc), tetrazolyl (e.g., 1H-tetrazolyl, 2H-tetrazolyl, etc), dihydrotriazinyl (e.g., 4,5-dihydro-1,2,4-triazinyl, 2,5-dihydro-1,2,4-triazinyl, etc), etc;

saturated 3 to 8-membered heteromonocyclic group containing 1 to 4 nitrogen atom(s), for example, pyrrolidinyl, imidazolidinyl, piperidyl (e.g. piperidino, etc), piperazinyl, etc;

unsaturated condensed heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc), dihydrotriazolopyridazinyl, etc;

unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc), etc;

saturated 3 to 8-membered heteromonocyclic group containing 1 to 2 oxygen atom(s) and 1 to 3 nitrogen atom(s), for example, morpholinyl, oxazolidinyl (e.g. 1,3-oxazolidinyl, etc), etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc;

saturated 3 to 8-membered heteromonocyclic group containing 1 to 2 sulfur atom(s) and 1 to 3 nitrogen atom(s), for example, thiazolidinyl, etc;

unsaturated 3 to 8-membered heteromonocyclic group containing a sulfur atom, for example, thienyl, etc;

unsaturated condensed heterocyclic group containing 1 to 2 sulfur atom(s) and 1 to 3 nitrogen atom(s), for example, benzothiazolyl, benzothiadiazolyl, etc;

unsaturated 3 to 8-membered heteromonocyclic group containing 1 to 2 oxygen atom(s), for example, furyl, pyranyl, dioxolyl, etc;

saturated 3 to 8-membered heteromonocyclic group containing 1 to 2 oxygen atom(s), for example, oxolanyl, tetrahydropyranyl (e.g. tetrahydro-2H-pyran-2-yl, etc), dioxolanyl, etc;

unsaturated condensed heterocyclic group containing 1 to 2 oxygen atom(s), for example, isobenzofuranyl, chromenyl (e.g. 2H-chromen-3-yl, etc), dihydrochromenyl (e.g. 3,4-dihydro-2H-chromen-4-yl, etc), etc; and the like.

Preferred example of "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" may be unsaturated 3 to 8-membered heteromonocyclic group containing 1 to 4 nitrogen atom(s); saturated 3 to 8-membered heteromonocyclic group containing 1 to 4 nitrogen atom(s); saturated 3 to 8-membered heteromonocyclic group containing 1 to 2 oxygen atom(s) and 1 to 3 nitrogen atom(s); and saturated 3 to 8-membered heteromonocyclic group containing 1 to 2 oxygen atom(s); in which the preferred one may be pyridyl, tetrazolyl, piperidyl, piperazinyl, morpholinyl, oxazolidinyl and tetrahydropyranyl; and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

"heterocyclic group" thus explained may have one or more (preferably 1 to 3) suitable substituent(s) such as hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc), aryl which may have lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc), oxo, or the like, in which preferred "suitable substituent(s)" may be hydroxy($C_1$–$C_4$)alkyl, phenyl having ($C_1$–$C_4$)alkoxy and oxo, and the more preferred one may be 2-hydroxyethyl, 2-methoxyphenyl and oxo.

Suitable "heterocyclic group" in "heterocyclic group which may have one or more suitable substituent(s)" can be referred to the ones exemplified for "heterocyclic group" of "lower alkyl having heterocyclic group, in which heterocyclic group may have one or more suitable substituent(s)" and "higher alkyl having heterocyclic group, in which heterocyclic group may have one or more suitable substituent(s)", and the preferred one may be unsaturated condensed heterocyclic group containing 1 to 2 oxygen atom(s), the more preferred one may be dihydrochromenyl, and the most preferred one may be 3,4-dihydro-2H-chromen-4-yl.

This "heterocyclic group" may have one or more (preferably 1 to 4) suitable substituent(s) such as aforesaid lower alkyl, hydroxy, cyano or the like, in which the preferred one may be ($C_1$–$C_4$)alkyl, hydroxy and cyano, and the most preferred one may be methyl, hydroxy and cyano.

Suitable "ar(lower)alkyl" may include mono- or di- or triphenyl(.lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc) and the like, in which the preferred one may be phenyl($C_1$–$C_4$) alkyl and the most preferred one may be benzyl.

Suitable "N-containing heterocyclic group" in "N-containing heterocyclic group which may have one or more suitable substituent(s)" may be heterocyclic group having at least one nitrogen atom as its ring member among the aforesaid "heterocyclic group", and said "N-containing heterocyclic group" may have one or more (preferably 1 to 3) suitable substituent(s) such as aforesaid hydroxy(lower)alkyl, aforesaid aryl which may have lower alkoxy, oxo or the like.

Suitable "tetrazolyl(lower)alkyl" may be 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl, or the like, in which the preferred one may be tetrazolyl($C_1$–$C_6$)alkyl and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-y1)pentyl and 6-(1H-tetrazol-5-yl)hexyl.

Suitable "tetrazolyl(higher)alkyl" may be 7-(1H-tetrazol-5-yl)heptyl, 8-(1H-tetrazol-5-yl)octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)tetradecyl, 15-(1H-tetrazol-5-yl)pentadecyl, 12-(1H-tetrazol-5-yl)hexadecyl, 17-(1H-tetrazol-1-yl)heptadecyl, 4-(1H-tetrazol-5-yl)octadecyl, 19-(1H-tetrazol-5-yl)nonadecyl, 1-(1H-tetrazol-1-yl)-12-ethylheptadecyl, 20-(1H-tetrazol-5-yl) icosyl, or the like, in which the preferred one may be tetrazolyl($C_7$–$C_{16}$)alkyl and the more preferred one may be 7-(1H-tetrazol-5-yl)heptyl, 8-(1H-tetrazol-5-yl)octyl, 9-(1H-tetrazol-5-yl)nonyl, 10-(1H-tetrazol-5-yl)decyl and 12-(1H-tetrazol-5-yl)dodecyl.

Suitable "hydroxy(lower)alkyl" may be the ones having 2 to 7 carbon atom(s) and having hydroxy at the terminal carbon atom such as 2-hydroxyethyl, 1-(hydroxymethyl) ethyl, 2-(hydroxymethyl)propyl, 1-(2-hydroxyethyl)ethyl, 5-hydroxypentyl, 3-(hydroxymethyl)pentyl, 2-(carboxymethyl)hexyl, or the like, in which the preferred one may be hydroxy($C_2$–$C_5$)alkyl and the most preferred one may be 2-hydroxyethyl.

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, external (topical), or oral or parenteral (including subcutaneous, intravenous and intramuscular) administrations.

The active ingredient may be compounded, for example, with the usual non-toxic, pharmaceutically acceptable carriers for tablets, pellets, troches, capsules, suppositories, solutions, emulsions, suspensions, and any other form suitable for use. And, if necessary, in addition, auxiliary, stabilizing, thickening and coloring agents and perfumes may be used.

The object compound (I) or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, or oral administration.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being or an animal, in case of oral administration, a daily dose of 0.001–200 mg of the object compound (I) per kg weight of a human being or an animal is generally given for the prevention and/or the treatment of aforesaid diseases in a human being or an animal.

In order to show the usefulness of the pyrazolopyridine compound (I) to be used in the present invention for the prevention and/or the treatment of anemia in a human being or an animal, the pharmacological test data of the representative compound thereof is shown in the following.

Test 1: Effect on Anemia in monkey

[I] Test Compound (1) 3-[2-(3-Carboxypropyl)-3-oxo-2,3-dihydropyridazin-6-yl]- 2-phenylpyrazolo[1,5-a]pyridine [the compound of Example 36 of EP-0379979, hereinafter referred to as Test Compound (1)]

[II] Test Method

Two groups of male Cynomolgus monkeys (weighing 5.2 to 6.8 kg) (4 monkeys per one group) were subcutaneously injected with 1.25% saline solution of phenylhydrazine hydrochloride (12.5 mg/kg) on days 1 and 3.

The test compound (1) (3.2 mg/kg) suspended in 0.5% methylcellulose in 2 ml/kg was administered orally twice a day [at 10 a.m. (hereinafter referred to as "0hr") and 4 p.m. (hereinafter referred to as "6hr")] for 5 consecutive days. For the control group, 0.5% methylcellulose (vehicle) was given instead of test compound (1).

Blood samples were drawn just before the administration of the test compound (1) (or vehicle) to measure hematocrit value and erythropoietin (EPO) level. EPO level was measured with the PIA kit commercially available from Chugai Pharmaceutical Co., Ltd.

[III] Test Results

Hematocrit value (%) and EPO level (mIU/ml) at each time were as follows.

| | Hematocrit value (%) | | | | | | | | | |
|---|---|---|---|---|---|---|---|---|---|---|
| | day | | | | | | | | | |
| | 1 | | 2 | | 3 | | 4 | | 5 | |
| group | 0 hr | 6 hr | 0 hr | 6 hr | 0 hr | 6 hr | 0 hr | 6 hr | 0 hr | 6 hr |
| control grop | 44 ± 1 | 42 ± 1 | 38 ± 1 | 37 ± 1 | 32 ± 1 | 27 ± 2 | 22 ± 2 | 22 ± 1 | 19 ± 2 | 19 ± 2 |
| test group | 43 ± 1 | 44 ± 2 | 43 ± 1 | 42 ± 2 | 37 ± 2 | 35 ± 2 | 29 ± 3 | 28 ± 2 | 25 ± 2 | 24 ± 2 |

| | EPO level (mIU/ml) | | | | | | | | | |
|---|---|---|---|---|---|---|---|---|---|---|
| | day | | | | | | | | | |
| | 1 | | 2 | | 3 | | 4 | | 5 | |
| group | 0 hr | 6 hr | 0 hr | 6 hr | 0 hr | 6 hr | 0 hr | 6 hr | 0 hr | 6 hr |
| control group | 10.0 ± 1.4 | 10.8 ± 1.6 | 19.2 ± 3.8 | 29.7 ± 11.7 | 59.4 ± 12.0 | 89.7 ± 18.4 | 166.3 ± 33.3 | 210.5 ± 31.0 | 245.8 ± 36.5 | 250.8 ± 39.0 |
| test group | 10.7 ± 0.9 | 14.6 ± 0.5 | 23.4 ± 2.9 | 34.9 ± 10.9 | 71.1 ± 19.9 | 114.5 ± 33.2 | 193.1 ± 22.0 | 203.2 ± 22.5 | 211.1 ± 35.3 | 272.2 ± 26.8 |

(each value was expressed in mean ± S.E.)

As shown in the above test data, the test compound (1) is useful for the prevention and/or the treatment of anemia.

Further, in the test group the anemia was improved in comparison with the control group, while the EPO level showed the similar patterns in both groups. This results mean when compared at the same hematocrit value, the EPO level in the test group was higher than that in the control group, that is, the production of EPO was increased in the test group.

The following Examples are given for the purpose of illustrating the preparation of the compound (Ia) in more detail.

EXAMPLE 1

Thionyl chloride (145 mg) was added dropwise to a stirred mixture of 3-(2-phenylpyrazolo[1,5-a]pyridin-3-yl) acrylic acid (trans isomer) (270 mg) and N,N-dimethylformamide (1 drop) in methylene chloride (1.5 ml) under ice-cooling. After being stirred at room temperature for 2 hours and 50 minutes, the solvent was evaporated in vacuo to give acid chloride derivative. The above acid chloride derivative was added by portions to a stirred mixture of (R)-2-(methoxycarbonylmethyl)piperidine hydrochloride (237 mg) and triethylamine (340 μl) in methylene chloride (1.5 ml) at −10° C.

The reaction mixture was stirred at room temperature overnight and then poured into ice-water (10 ml). The mixture was extracted with methylene chloride (20 ml×2). The combined extracts were washed with 0.1N HCl (10 ml), 10% aq K$_2$CO$_3$ (10 ml) and brine (10 ml), dried over sodium sulfate and evaporated in vacuo to give crude material, which was purified by column chromatography on silica gel (10 g) with a mixture of ethyl acetate and methylene chloride (1:10) as an eluent to give (2R)-1-[3-(2-phenylpyrazolo[1,5-a]pyridin-3-yl)acryloyl]-2-(methoxycarbonylmethyl) piperidine (trans isomer) (330 mg) as an oil.

$[\alpha]_D^{19}$=+65.11° (C=1.8, MeOH)

IR (Film): 1730, 1635, 1590, 1515 cm$^{-1}$

NMR (CDCl$_3$, δ): 1.33–1.77 (7H, m), 2.61 (1H, dd, J=14.7 and 7.1 Hz), 2.76 (1H, brd s), 3.66 (3H, s), 4.76 (1H, brd s), 6.90 (1H, td, J=6.9 and 1.2 Hz), 7.35 (1H, t, J=7.4 Hz), 7.43–7.55 (3H, m), 7.72 (1H, dd, J=7.7 and 1.7 Hz), 7.95 (1H, d, J=15.5 Hz), 8.53 (1H, d, J=6.9 Hz)

MS: m/e 403 (M$^+$)

EXAMPLE 2

(2RS)-1-[3-(2-Phenylpyrazolo[1,5-a]pyridin-3-yl) acryloyl]-2-(methoxycarbonylmethyl)piperidine (trans isomer) was obtained according to a similar manner to that of Example 1.

IR (Film) : 1730, 1635, 1590, 1510 cm$^{-1}$

NMR spectrum was the same as that of the compound of Example 1.

EXAMPLE 3

A mixture of (2R)-1-[3-(2-phenylpyrazolo[1,5-a]pyridin-3-yl)acryloyl]-2-(methoxycarbonylmethyl)piperidine (trans isomer) (210 mg) and 1N sodium hydroxide solution (0.573 ml) in methanol (2.0 ml) was heated to reflux for 2 hours. Methanol was evaporated in vacuo and water (20 ml) was added in the residue. The solution was acidified with 1N hydrochloric acid and extracted with methylene chloride (10 ml×2). The combined extracts were washed with brine (10 ml), dried over sodium sulfate and evaporated in vacuo. The crude crystals were recrystallized from a mixture of ethyl acetate and diethyl ether to give colorless crystals of (2R)-1-[3-(2-phenylpyrazolo[1,5-a]pyridin-3-yl)acryloyl]-2-(carboxymethyl)piperidine (trans isomer) (152.7 mg).

mp: 165°–166° C.

$[\alpha]_D^{18}$=+72.75° (C=1.09, MeOH)

IR (Nujol): 1715, 1625, 1570, 1510 $cm^{-1}$

NMR (CDCl$_3$, δ): 1.36–1.82 (7H, m), 2.57 (1H, dd, J=15.1 and 6.4 Hz), 2.67–3.25 (2H, m), 4.69 (1H, brd s), 6.40–7.34 (2H, m), 7.37–7.51 (4H, m), 7.65–7.77 (3H, m), 7.89 (1H, d, J=15.5 Hz), 8.44 (1H, brd s), 10.40 (1H, brd s)

Analysis Calcd. for $C_{23}H_{23}N_3O_3$: C 70.93, H 5.95, N 10.79 Found: C 70.81, H 5.97, N 10.66

EXAMPLE 4

(2RS)-1-[3-(2-Phenylpyrazolo[1,5-a]pyridin-3-yl) acryloyl]-2-(carboxymethyl)piperidine (trans isomer) was obtained according to a similar manner to that of Example 3.

mp: 132°–134° C.

IR (Nujol): 1705, 1625, 1560, 1505 $cm^{-1}$

NMR spectrum was the same as that of the compound of Example 3.

EXAMPLE 5

A solution of dimethyl sulfoxide (202 mg) in methylene chloride (1.0 ml) was added dropwise to a solution of oxalyl dichloride (247 mg) in methylene chloride (10 ml) over 5 minutes at –78° C. After 10 minutes, a solution of (2R)-1-[3-(2-phenylpyrazolo[1,5-a]pyridin-3-yl)acryloyl]-2-(2-hydroxyethyl)piperidine (trans isomer) (364 mg) in methylene chloride (3.4 mg) was added dropwise over 10 minutes at –78° C. The solution was stirred at –78° C. for 20 minutes and at –45° C. for 1 hour. Triethylamine (986 µl) was added to the solution and the mixture was stirred at –20°~0° C. for 20 minutes. Saturated ammonium chloride solution (20 ml) was added to the reaction mixture was the mixture was extracted with methylene chloride (10 ml×2). The combined extracts were washed with brine (10 ml), dried over magnesium sulfate and evaporated in vacuo. The crude material was purified by column chromatography on silica gel (10 g) with a mixture of methylene chloride and ethyl acetate (10:1) as an eluent to give (2R)-1-[3-(2-phenylpyrazolo[1,5-a]pyridin-3-yl)acryloyl]-2-(formylmethyl)piperidine (trans isomer) (139.0 mg) as an oil.

$[\alpha]_D^{17}$=+35.41° (C=1.44 MeOH)

IR (Film): 1720, 1640, 1590, 1520 $cm^{-1}$

NMR (CDCl$_3$, δ): 1.05–2.10 (8H, m), 2.22–3.12 (3H, m), 6.50–6.93 (2H, m), 7.05–7.54 (4H, m), 7.67–7.81 (3H, m), 7.93 (1H, d, J=15.4 Hz), 8.45–8.53 (1H, m), 9.68–9.75 (1H, m)

EXAMPLE 6

Thionyl chloride (0.2 ml) was added dropwise to a solution of methylene chloride (dry, 40 ml) and N,N-dimethylformamide (0.2 ml) at 0° C. and stirred for 30 minutes. To this cooled solution was added (2R)-1-[3-(2-phenylpyrazolo[1,5-a]pyridin-3-yl)acryloyl]-2-(carboxymethyl)piperidine (trans isomer) (1.0 g) and the mixture was stirred for 1.5 hours. To this solution was added a solution of 28% aqueous ammonia solution (20 ml) and stirring was continued for further 2 hours. The aqueous and organic phases were separated and the organic layer was evaporated. The oily residue was subjected to column chromatography (silica gel, 60 mesh) using ethyl acetate as eluent. Evaporation of the solvent afforded (2R)-1-[3-(2-phenylpyrazolo[1,5-a]pyridin-3-yl)acryloyl]-2-(carbamoylmethyl)piperidine (trans isomer) (405 mg) as a white granular solid.

mp: 195°–197° C.

IR (Nujol): 3440, 3160, 1675, 1645 $cm^{-1}$

NMR (CDCl$_3$, δ): 1.6–1.7 (7H, m), 2.47 (1H, dd, J=5.1 and J=15.9 Hz), 2.7 (1H, brd d), 3.15 (0.25H, brd t), 3.75 (0.3H, brd s), 5.31 (1H, brd d), 6.69 (0.5H, d, J=15.43 Hz), 6.92 (1H, t, J=5.63 Hz), 7.5 (5H, m), 7.68 (2H, dd, J=1.87 and J=7.6 Hz), 7.94 (1H, d, J=15.43 Hz), 8.53 (1H, d, J=6.9 Hz)

MS: m/e 388 (M$^+$), 329, 247, 219, 218, 217, 141

Analysis Calcd. for $C_{23}H_{24}N_4O_2$ 388.468 C 71.1, H 6.2, N 14.4 Found: C 70.6, H 6.4, N 14.3

The following compounds (Examples 7 and 8) were obtained according to a similar manner to that of Example 6.

EXAMPLE 7

(2R)-1-[3-(2-phenylpyrazolo[1,5-a]pyridin-3-yl) acryloyl]-2-(N-ethylcarbamoylmethyl)piperidine (trans isomer)

mp: 141°–143° C.

IR (Nujol): 3500, 3450, 3300, 1655, 1640 $cm^{-1}$

NMR (CDCl$_3$, δ): 1.09 (3H, t, J=7.27 Hz), 1.5 brd s), 1.64 (1H, s), 1.7 (6H, m), 2.45 (1H, dd, J=5.0 and J=15.17 Hz), 2.75 (0.6H, brd s), (2H, m), 4.76 (0.25H, brd d), 5.15 (0.25H, brd d), 6.66 (0.3H, d, J=15.3 Hz), 6.91 (1H, t, J=6.25 Hz), 7.28–7.68 (8H, m), 7.8 (1H, d, J=15.30 Hz), 8.52 (1H, d, J=6.91 Hz)

MS: m/e 416 (M$^+$), 329, 245, 219, 169

Analysis Calcd. for $C_{25}H_{28}N_4O_2 \cdot 1/2H_2O$ C 70.56, H 6.87, N 13.16 Found: C 70.23, H 6.99, N 13.03

EXAMPLE 8

(2R)-1-[3-(2-Phenylpyrazolo[1,5-a]pyridin-3-yl) acryloyl]-2-(N,N-diethylcarbamoylmethyl)piperidine (trans isomer)

IR (CHCl$_3$): 3700, 3500, 1643, 1600 $cm^{-1}$

NMR (CDCl$_3$, δ): 1.08 (3H, t, J=7.1 Hz), 1.18 (3H, t, J=7.1 Hz), 1.72 (7H, m), 2.6 (2H, m), 3.33 (4H, m), 5.10 (1H, brd s), 6.90 (1H, t, J=5.58 Hz), 7.46 (4H, m), 7.69 (2H, dd, J=6.23 and 7.7 Hz), 7.91 (1H, d, J=15.3 Hz), 8.2 (0.25H, brd s), 8.52 (1H, d, J=6.92 Hz)

MS: m/e 444 (M$^+$), 325, 247, 219, 197

EXAMPLE 9

A solution of (2R)-1-[3-(2-phenylpyrazolo[1,5-a]-pyridin-3-yl)acryloyl]-2-(carboxymethyl)piperidine (trans isomer) (5.73 g) in methanol (287 ml) was irradiated with sunlight for 32 hours. The yellow crystals were separated by filtration, washed with methanol, and dried under vacuum to give 4.97 g of its cis isomer. A suspension of this cis isomer (4.88 g) in methanol (350 ml) was heated to reflux and cooled to room temperature. The precipitates were collected by filtration, washed with methanol, and dried under vacuum to give yellow prisms of (2R)-1-[3-(2-phenylpyrazolo[1,5-a]pyridin-3-yl)acryloyl]-2-(carboxymethyl)piperidine (cis isomer) (4.20 g).

mp: 195°–196° C.

IR (Nujol): 1715, 1625, 1570, 1525 $cm^{-1}$

NMR (DMSO-d$_6$, δ): 0.40–1.60 (6H, m), 2.07 (0.5H, dd, J=15.1 and J=5.1 Hz), 2.90 (0.5H, t, J=12.5 Hz), 3.34 (1H, brd s), 3.74 (0.5H, brd d, J=13.3 Hz), 4.23 (0.5H, brd d, J=13.3 Hz), 4.42–4.59 (0.5H, m), 4.70–4.90 (0.5H, m), 6.20 (0.5H, d, J=12.0 Hz), 6.22 (0.5H, d, J=12.0 Hz), 6.75 (0.5H, d, J=12.0 Hz), 6.81 (0.5H, d, J=12.0 Hz), 6.97 (1H, t, J=6.6

Hz), 7.31 (1H, t, J=7.9 Hz), 7.41–7.55 (4H, m), 7.76–7.79 (2H, m), 8.74 (1H, d, J=6.9 Hz), 12.29 (1H, brd s)

Analysis Calcd. for $C_{23}H_{23}N_3O_3$: C 70.93, H 5.95, N 10.79 Found: C 70.74, H 6.05, N 10.76

The following compounds (Examples 10 to 16) were obtained according to a similar manner to that of Example 1.

EXAMPLE 10

(2R)-1-[3-(2-Phenylpyrazolo[1,5-a]pyridin-3-yl) acryloyl]-2-(carboxymethyl)piperidine (trans isomer)

mp: 165°–166° C.

$[\alpha]_D^{18}$=+72.75° (C=1.09, MeOH)

IR (Nujol) : 1715, 1625, 1570, 1510 $cm^{-1}$

EXAMPLE 11

(2RS)-1-[3-(2-Phenylpyrazolo[1,5-a]pyridin-3-yl) acryloyl]-2-(carboxymethyl)piperidine (trans isomer)

mp: 132°–134° C.

IR (Nujol) : 1705, 1625, 1560, 1505 $cm^{-1}$

EXAMPLE 12

(2R)-1-[3-(2-Phenylpyrazolo[1,5-a]pyridin-3-yl) acryloyl]-2-(formylmethyl)piperidine (trans isomer)

$[\alpha]_D^{17}$=+35.41° (C=1.44 MeOH)

IR (Film) 1720, 1640, 1590, 1520 $cm^{-1}$

EXAMPLE 13

(2R)-1-[3-(2-Phenylpyrazolo[1,5-a]pyridin-3-yl) acryloyl]-2-(carbamoylmethyl)piperidine (trans isomer)

mp: 195°–197° C.

IR (Nujol) : 3440, 3160, 1675, 1645 $cm^{-1}$

EXAMPLE 14

(2R)-1-[3-(2-Phenylpyrazolo[1,5-a]pyridin-3-yl) acryloyl]-2-(N-ethylcarbamoylmethyl)piperidine (trans isomer)

mp: 142°–143° C.

IR (Nujol): 3500, 3450, 3300, 1655, 1640 $cm^{-1}$

EXAMPLE 15

(2R)-1-[3-(2-Phenylpyrazolo[1,5-a]pyridin-3-yl) acryloyl]-2-(N,N-diethylcarbamoylmethyl)piperidine (trans isomer)

IR (CHCl$_3$): 3700, 3500, 1643, 1600 $cm^{-1}$

EXAMPLE 16

(2R)-1-[3-(2-Phenylpyrazolo[1,5-a]pyridin-3-yl) acryloyl]-2-(carboxymethyl)piperidine (cis isomer)

mp: 195°–196° C.

IR (Nujol) : 1715, 1625, 1570, 1525 $cm^{-1}$

We claim:

1. A method for the prevention and/or the treatment of anemia by raising the erythropoietin level in a patient in need thereof, which comprises administering a pyrazolopyridine compound of the following formula, or a pharmaceutically acceptable salt thereof, to a human being or an animal:

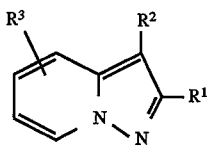

wherein
$R^1$ is lower alkyl, aryl which may have one or more suitable substituent(s) selected from the group consisting of halogen, lower alkoxy, nitro, amino and protected amino or a heterocyclic group, $R^2$ is a group of the formula:

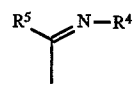

wherein
$R^4$ is protected amino or hydroxy and $R^5$ is hydrogen or lower alkyl;
cyano;
a group of the formula:

wherein $R^6$ is an acyl group, or a group of the formula:

wherein $R_N$ is N-containing heterocyclic group which may have one or more suitable substituent(s) selected from the group consisting of lower alkyl, lower alkoxy(lower) alkyl, acyloxy(lower) alkyl, carboxy, protected carboxy and acyl(lower) alkyl, and A is lower aliphatic hydrocarbon group which may have one or more halogens;
amidated carboxy; unsaturated heterocyclic group which may have one or more suitable substituent(s) selected from the group consisting of lower alkyl; lower alkyl having hydroxy and halogen; hydroxy (lower) alkyl; lower alkoxy(lower)alkyl; carboxy (lower) alkyl; protected carboxy(lower)alkyl; protected carboxy(lower)alkyl; amino(lower)alkyl; lower alkylamino(lower)alkyl; carboxy(lower) alkylamino(lower)alkyl; protected carboxy(lower) alkylamino(lower)alkyl; lower alkylamino(lower) alkyl having hydroxy and aryloxy; protected amino (lower)alkyl; cyano(lower)alkyl; cyano(higher) alkyl; lower alkyl having heterocyclic group, in which heterocyclic group may have one or more suitable substituent(s) selected from the group consisting of hydroxy(lower)alkyl, aryl which may have lower alkoxy and oxo; higher alkyl having heterocyclic group, in which heterocyclic group may have one or more suitable substituent(s) selected from the group consisting of hydroxy(lower)alkyl, aryl which may have lower alkoxy and oxo; ar(lower)alkyl; lower alkyl; heterocyclic group which may have one or more suitable substituent(s) selected from the group consisting of lower alkyl, hydroxy and cyano; carboxy(lower)alkenyl; amino; di(lower) alkylamino; halogen; lower alkoxy; oxo; hydroxy; cyano; carboxy; protected carboxy and lower alkanoyl; amino or protected amino; and $R^3$ is hydrogen, lower alkyl, lower alkoxy or halogen.

2. The method of claim 1, wherein
$R^1$ is lower alkyl, phenyl which may have one or more suitable substituent(s) selected from the group consisting of halogen, lower alkoxy, nitro, amino and protected amino or unsaturated 3 to 8 membered heteromonocyclic group containing 1 to 4-nitrogen atom(s),
$R^2$ is a group of the formula:

$$\underset{\displaystyle|}{\overset{R^5\diagdown\quad\diagup N-R^4}{\phantom{X}}}$$

wherein
$R^4$ is protected amino or hydroxy and $R^5$ is hydrogen or lower alkyl;
cyano;
a group of the formula:

—A—$R^6$ wherein $R^6$ is lower alkanoyl; carboxy; protected carboxy; or a group of the formula:

—$COR_N$ wherein $R_N$ is saturated 3 to 8 membered heteromonocyclic group containing 1 to 4 nitrogen atom(s); saturated condensed heterocyclic group containing 1 to 4 nitrogen atom(s); or saturated 3 to 8 membered heteromonocyclic group containing 1 to 2 oxygen atom(s) and 1 to 3 nitrogen atom(s), each of which may have one or more suitable substituent(s) selected from the group consisting of lower alkyl, lower alkoxy(lower)alkyl, acyloxy(lower)alkyl, acyl(lower) alkyl, carboxy and protected carboxy, and A is lower alkyl, lower alkenyl or lower alkynyl, each of which may have one or more halogen, or unsaturated 3 to 8 membered heteromonocyclic group containing 1 to 4 nitrogen atom(s) which may have 1 to 4 suitable substituent(s) selected from the group consisting of lower alkyl; lower alkyl having hydroxy and halogen; hydroxy(lower)alkyl; lower alkoxy(lower)alkyl; carboxy(lower)alkyl; protected carboxy(lower)alkyl; amino(lower)alkyl; lower alkylamino(lower)alkyl; carboxy(lower)alkylamino (lower)alkyl; protected carboxy(lower)alkylamino (lower)alkyl; lower alkylamino(lower)alkyl having hydroxy and aryloxy; protected amino(lower)alkyl; cyano(lower)alkyl; cyano(higher)alkyl; lower alkyl having heterocyclic group, in which heterocyclic group may have one or more suitable substituent(s) selected from the group consisting of hydroxy (lower)alkyl, aryl which may have lower alkoxy and oxo; higher alkyl having heterocyclic group, in which heterocyclic group may have one or more suitable substituent(s) selected from the group consisting of hydroxy(lower)alkyl, aryl which may have lower alkoxy and oxo; ar(lower)alkyl; lower alkyl; heterocyclic group which may have one or more suitable substituent(s) selected from the group consisting of lower alkyl, hydroxy and cyano; carboxy (lower)alkenyl; amino; di(lower)alkylamino; halogen; lower alkoxy; oxo; hydroxy; cyano; carboxy; protected carboxy and lower alkanoyl.

3. The method of claim 2, wherein
$R^1$ is phenyl,
$R^2$ is a group of the formula:

—A—$R^6$ wherein
$R^6$ is a group of the formula:

—$COR_N$ wherein $R_N$ is piperidino, pyrrolidin-1-yl, perhydroazepin-1-yl, piperazin-1-yl, morpholino, 7-azabicyclo [2.2.1]heptan-7-yl, or 3-azabicyclo [3.2.2]nonan-3-yl, each of which may have 1 to 4 suitable substituent (s) selected from the group consisting of lower alkyl, lower alkoxy(lower)alkyl, lower alkanoyloxy(lower)alkyl, lower alkanoyl (lower)alkyl, carboxy(lower)alkyl, lower alkoxycarbonyl(lower)alkyl, lower alkoxycarbonyl and carboxy, and A is as defined in claim 2;
pyridazinyl, dihydropyridazinyl, tetrahydropyridazinyl, pyrimidinyl, dihydropyrimidinyl, pyridyl, dihydropyridyl, tetrahydropyridyl, pyrazolyl or imidazothiadiazolyl, each of which may have 1 to 4 suitable substituent (s) selected from the group consisting of lower alkyl; lower alkyl having hydroxy and halogen; hydroxy (lower)alkyl; lower alkoxy(lower)alkyl; carboxy (lower)alkyl; protected carboxy(lower)alkyl; amino (lower)alkyl; lower alkylamino(lower)alkyl; carboxy(lower)alkylamino(lower)alkyl; protected carboxy(lower)alkylamino(lower)alkyl; lower alkylamino(lower)alkyl having hydroxy and aryloxy; protected amino(lower)alkyl; cyano(lower) alkyl; cyano(higher)alkyl; lower alkyl having heterocyclic group, in which heterocyclic group may have one or more suitable substituent(s) selected from the group consisting of hydroxy(lower)alkyl, aryl which may have lower alkoxy and oxo; higher alkyl having heterocyclic group, in which heterocyclic group may have one or more suitable substituent(s) selected from the group consisting of hydroxy (lower) alkyl, aryl which may have lower alkoxy and oxo; ar(lower)alkyl; lower alkenyl; heterocyclic group which may have one or more suitable substituent(s) selected from the group consisting of lower alkyl, hydroxy and cyano; carboxy(lower) alkenyl; amino; di(lower) alkylamino; halogen; lower alkoxy; oxo; hydroxy; cyano; carboxy; protected carboxy and lower alkanoyl; and
$R^3$ is hydrogen.

4. The method of claim 3, wherein
$R^2$ is a group of the formula:

—A—$R^6$ wherein
$R^6$ is a group of the formula:

—$COR_N$ wherein $R_N$ is piperidino which may have 1 to 4 suitable substituent(s) selected from the group consisting of lower alkyl, lower alkoxy(lower)alkyl, lower alkanoyloxy(lower)alkyl, lower alkanoyl (lower)alkyl, carboxy(lower)alkyl, lower alkoxycarbonyl(lower)alkyl, lower alkoxycarbonyl and carboxy, and A is as defined in claim 3,
or dihydropyridazinyl which may have 1 to 4 suitable substituent(s) selected from the group consisting of lower alkyl; lower alkyl having hydroxy and halogen; hydroxy(lower)alkyl; lower alkoxy(lower)alkyl; carboxy(lower)alkyl; protected carboxy (lower)alkyl; amino(lower)alkyl; lower alkylamino (lower)alkyl; carboxy(lower)alkylamino(lower) alkyl; protected carboxy(lower)alkylamino(lower) alkyl; lower alkylamino(lower)alkyl having hydroxy and aryloxy; protected amino(lower)alkyl; cyano (lower)alkyl; cyano(higher) alkyl; lower alkyl having heterocyclic group, in which heterocyclic group may have one or more suitable substituent(s) selected from the group consisting of hydroxy (lower)alkyl, aryl which may have lower alkoxy and oxo; higher alkyl having heterocyclic group, in which heterocyclic group may have one or more suitable substituent(s) selected from the group consisting of hydroxy(lower)alkyl, aryl which may have lower alkoxy and oxo; ar(lower)alkyl; lower alkenyl; heterocyclic group which may have one or more suitable substituent(s) selected from the group consisting of lower alkyl, hydroxy and cyano; carboxy (lower)alkenyl; amino; di(lower) alkylamino; halogen; lower alkoxy; oxo; hydroxy; cyano; carboxy; protected carboxy and lower alkanoyl.

5. The method of claim 4, wherein $R^2$ is a group of the formula:

—A—$R^6$ wherein
$R^6$ is a group of the formula:

—$COR_N$ wherein $R_N$ is piperidino having carboxy(lower)alkyl, and

A is lower alkenyl, or dihydropyridazinyl having carboxy(lower)alkyl and oxo.

6. The method of claim 5, wherein the pyrazolopyridine compound is selected from the group consisting of: (2R)-1-{3-(2-phenylpyrazolo{1,5}-a}pyridin-3-yl)acryloyl}-2-(carboxymethyl)piperidine (trans isomer), and 3-{2-(3-carboxypropyl)-3-oxo-2,3-dihydropyridazin-6-yl}-2-phenylpyrazolo{1,5 - a}pyridine.

* * * * *